United States Patent [19]

Bailey

[11] Plant 4,830

[45] Mar. 16, 1982

[54] ROSE PLANT

[75] Inventor: Dorothy J. S. Bailey, Bakersfield, Calif.

[73] Assignee: San Joaquin Rose Co., McFarland, Calif.

[21] Appl. No.: 185,376

[22] Filed: Sep. 8, 1980

[51] Int. Cl.[3] ..... A01H 5/00

[52] U.S. Cl. ..... Plt./11

[58] Field of Search ..... Plt./11

*Primary Examiner*—James R. Feyrer

*Attorney, Agent, or Firm*—Vincent G. Gioia

[57] ABSTRACT

A new hybrid tea rose variety of many petaled blooms of ivory and red coloring.

1 Drawing Figure

The present invention relates to a new and distinct variety of rose plant of the hybrid tea rose class, which was originated by my crossing as seed parent my seedling of (Kordes Perfecta × Queen Elizabeth) and the rose known as "Mr. Lincoln" as pollen parent.

Among the novel characteristics possessed by this new variety which distinguish it from its parents and all other varieties of which I am aware are many petaled blooms borne on a vigorous, tall, upright growing plant. The flowers have ivory petal undersurface with pinkish cast and red top surface coloring which predominates as blooms open and mature. Asexual reproduction by budding of the new variety as performed in Kern County, Calif., shows that the foregoing and other distinguishing characteristics come true to form and are established and transmitted through succeeding propagations.

The new and improved rose variety which I have developed features large, many-petaled flowers of pleasing ivory and red coloring displayed on a vigorous, upright, free branching plant with abundant disease resistant foliage. The plant grows well even in the first season attaining a height of 4 to 5 feet.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "42C" is plate 42C of the Royal Horticultural Society Color Chart.

Parentage: Seedling.

*Seed parent.*—My unpatented, unreleased seedling of (Kordes Perfecta × Queen Elizabeth).

*Pollen parent.*—"Mr. Lincoln".

Class: Hybrid tea.

The following observations are made of specimens grown outdoors in Kern County, Calif. during the month of October.

FLOWER

Blooming habit: Recurrent.

A. Bud:

(1) *Size.*—Large.

(2) *Form.*—Pointed.

(3) *Color.*—After speals fall, ivory colored petal undersurface (near to 19D with pink cast) of main portion of the petal is first visible, however, red colored petal edge (between 42C and 42D) of the petal under surface may also be seen. The red edge coloring varies from only at petal edge to extension further into the petal from the edge.

(4) *Sepals.*—Uniform spear shaped extending to the length of the bud.

(5) *Peduncle.*—Length — about $3\frac{1}{3}$ inches. Aspect — straight, smooth. Strength — erect. Color — near 146B.

B. Bloom:

(1) *Size.*—Average size when fully expanded — about $4\frac{1}{2}$ to 5 inches.

(2) *Borne.*—Singly and several together.

(3) *Form.*—High centered, recurving becoming ruffled.

(4) *Petalage.*—Number of petals under normal conditions — about 60.

(5) *Color.*—As buds open ivory colored petal undersurface becomes less visible and red colored petal top surface predominates. The red coloring varies from 42C and 42D to near 47A. However, open blooms upon aging lighten somewhat and feature 37B and 37C tonality. The red coloring which may appear at the edge of the petal undersurface is lighter toned than the red coloring of the petal top surface, perhaps due to washing of the ivory coloring into the red.

C. Petals:

(1) *Texture.*—Thick.

(2) *Appearance.*—Velvety sheen on top surface.

(3) *Form.*—With rounded edges.

(4) *Arrangement.*—Imbricated.

(5) *Petaloids in center.*—6 to 8.

(6) *Persistence.*—Drop off cleanly.

(7) *Fragrance.*—Slight.

(8) *Lasting quality.*—Good lasting quality on plant and as cut flower.

REPRODUCTIVE ORGANS

A. Stamens, filaments and anthers:

(1) *Arrangement.*—Stamens irregularly arranged around styles.

(2) *Color.*—22A.

B. Pollen:

*Color.*—20B.

C. Styles: Bunched, uneven.

D. Stigmas:

*Color.*—26C.

E. Hips:

*Shape.*—Globular.

*Size.*—Medium.

*Color.*—22A.

*Do seeds protrude?*—Yes.

PLANT

A. Form: Upright, tall.

B. Growth: Very vigorous, good branching from base.

*Height attained.*—About 4 to 5 feet first season.

C. Foliage: Compound 5 to 7 leaflets.

(1) *Size.*—Large.

(2) *Quantity.*—Very abundant.

(3) *Color.*—New foliage: Upper side — near to 137C with reddish blending; under side — near to 139C with some 158A. Old foliage: Upper side — between 136A and 146A; under side — near 147C.

(4) *Shape.*—Oval.

(5) *Texture.*—Upper side is leathery, glossy and under side is veined and textured.

(6) *Edge.*—Serrated.

(7) *Serration.*—Small.

(8) *Leaf stem.*—Color — near to 137A. Under side — 146D.

(9) *Stipules.*—Medium, bearded.

(10) *Resistance to disease.*—Blackspot — very resistant. Mildew — very resistant. Rust — very resistant.

D. Wood:

(1) *New wood.*—Color — near 146B. Bark — smooth.

(2) *Old wood.*—Color — near 146A with red cast. Bark — smooth.

E. Thorns:

(1) *Thorns.*—Quantity (main stalk) — ordinary. On laterals from stalk — normal. Form — flat. Length — medium. Color — 146C. Position — scattered.

(2) *Prickles.*—Normal.

F. Winter hardiness: Good winter hardiness.

I claim:

1. A new and distinct variety of rose plant of the hybrid tea class, substantially as shown and described, characterized particularly by large, many petaled flowers of ivory and red coloring borne on a vigorous, upright growing plant.

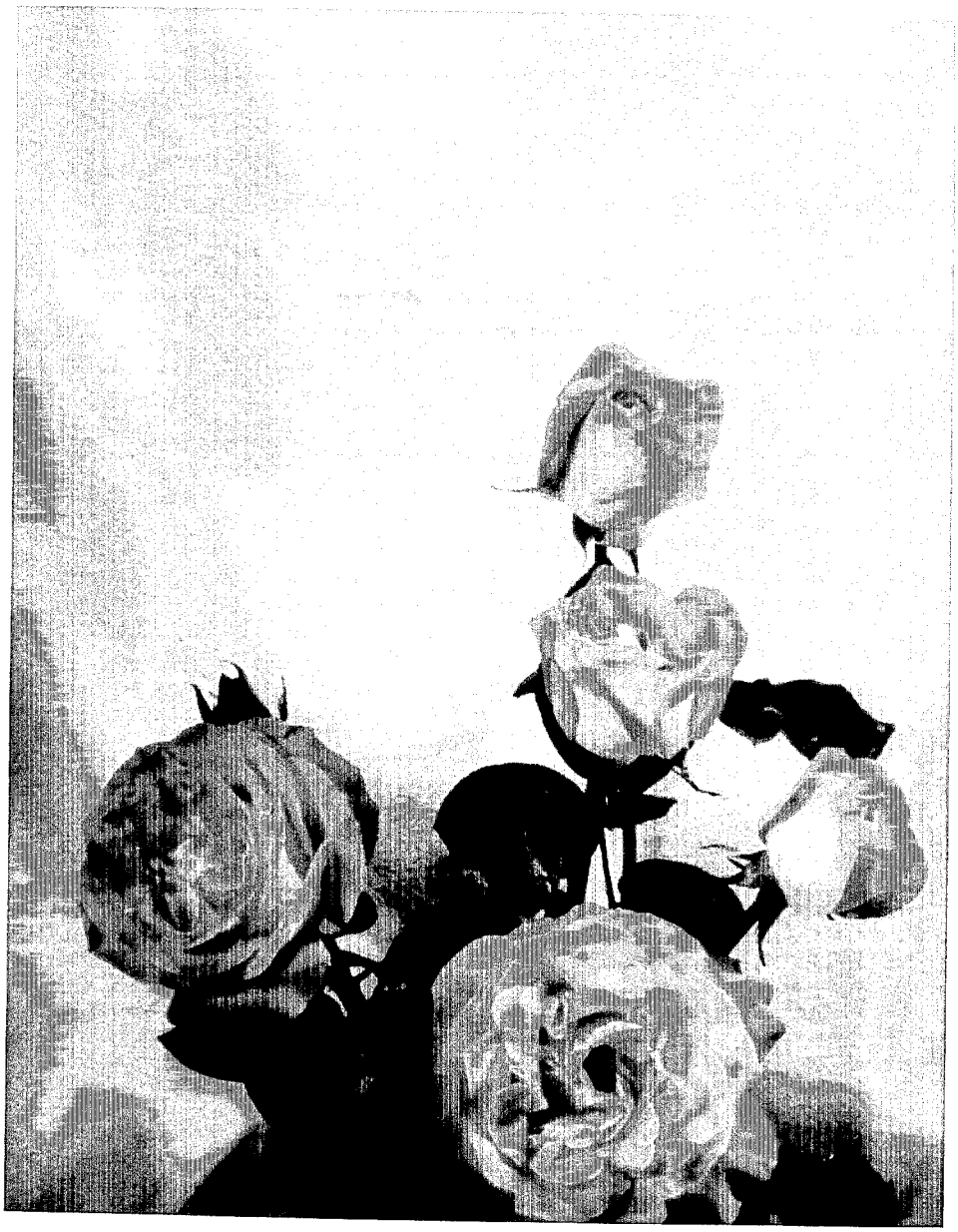

* * * * *